United States Patent
Sharma

(10) Patent No.: US 7,005,297 B2
(45) Date of Patent: Feb. 28, 2006

(54) USE OF NEUROACTIVE COMPOUNDS

(75) Inventor: Abhay Sharma, Delhi (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/798,223

(22) Filed: Mar. 11, 2004

(65) Prior Publication Data
US 2005/0144656 A1   Jun. 30, 2005

(30) Foreign Application Priority Data
Dec. 30, 2003   (WO) ...................... PCT/IN03/00418

(51) Int. Cl.
*C12N 5/00* (2006.01)
*A01K 67/00* (2006.01)

(52) U.S. Cl. .......................................... 435/375; 800/8

(58) Field of Classification Search ................ 435/375; 800/8
See application file for complete search history.

*Primary Examiner*—David Guzo
*Assistant Examiner*—Quang Nguyen
(74) *Attorney, Agent, or Firm*—Ladas & Parry LLP

(57) ABSTRACT

The invention relates to a novel use of neuroactive compounds by treating the fruitfly *Drosophila melanogaster* adult males with fly medium containing either of the neuroactive compounds strychnine, pentylenetetrazol, tetraethylammonium chloride, lithium carbonate and nicotine, crossing the drug treated males with untreated females to obtain progenies and self-crossing the progenies to obtain grand progenies, observing the locomotor behavior of the parents and their progenies and grand progenies in terms of height climbed in a negative geotaxis assay, wherein an altered height climbed by parents and their progenies and grand progenies, compared to those of normally fed males, demonstrates that the neuroactive compounds produce inheritable behavioral change.

1 Claim, No Drawings

USE OF NEUROACTIVE COMPOUNDS

FIELD OF THE INVENTION

The present invention relates to a novel use of neuroactive compounds in producing inheritable change in behavior. More particularly, the present invention relates to a novel use of neuroactive compounds in producing inheritable change in the locomotor behavior of the fruitfly *Drosophila melanogaster*.

By studying the effect of structurally and functionally diverse neuroactive drugs on locomotor behavior in drug exposed flies and their progenies and grand progenies which were never exposed to any drug at any time, it is demonstrated that drug induced alteration in locomotor behavior is inheritable. This inheritable behavioral effect of neuroactive drugs can be put to a novel use. For example, it can be used in animal breeding to epigenetically alter behavioral characteristics of the organism.

BACKGROUND AND PRIOR ART

The Lamarckian theory of inheritance of acquired characters has mostly remained unaccepted in mainstream biology due to the lack of irrefutable experimental evidence as well as insufficient explanatory support against the Weismann's doctrine of isolation of the germ line from soma (1–3). Interestingly, there has been of late a revival of interest in some sort of Lamarckism (4, 5). Recently, pattern of gene expression regulated by chromatin factors has been found to be inherited through germ line (6). Both repressing and activating modes of gene regulation are inherited mitotically throughout development as well as through meiosis. Further, alteration in chromatin state induced by a drug that reduces function of a heat-shock chaperone protein has most recently been found to be inheritable and to underlie morphological alterations in *Drosophila* (7). The present work is based on the concept that drug induced behavioral alteration in an established model organism like *Drosophila* may suitably be used as an adaptive response to test the validity of Lamarckism.

Chronic exposure to neuroactive drugs including those of human use and abuse produces long lasting changes in neuronal function and behavior (8–10). Neural plasticity underlies these changes (10–11). Most important, involvement of regulation of gene expression and chromatin structure has recently been demonstrated in synaptic plasticity (12). *D. melanogaster* has lately emerged as an attractive model to study drug induced behavior and addiction (13–14). Exposure to various neuroactive compounds is known to affect locomotor behavior in both *Drosophila* as well as mammalian models (14–16). Like mammals, dopaminergic pathways in *Drosophila* play a role in modulating locomotor behavior in response to neuroactive drugs (17). Of the present interest was to know if neuroactive drugs cause inheritable alteration in locomotor behavior in *Drosophila*. That the drugs cause altered locomotor activity is known (Sharma, 2003, a rapid procedure for screening of neuroactive substance using the fruitfly *Drosophila melanogaster*, patent applied; 14–16). Here, I examined if chronic exposure of flies to a range of neuroactive compounds including addictive, convulsant, and mood stabilizing drugs induce an inheritable change in locomotor behavior by systematically surveying two subsequent generations of drug exposed flies to see if they also exhibit abnormal locomotor behavior.

OBJECTS OF THE INVENTION

The main object of the invention is a novel use of neuroactive drugs.

It is a further object of the invention to unravel a novel use of neuroactive drugs using the fruit fly *Drosophila melanogaster*.

It is another object of the invention to use neuroactive drugs in producing inheritable behavioral alteration.

It is a further object of the invention to use neuroactive drugs for producing epigenetically altered organism.

It is a further object of the invention to use neuroactive drugs for producing behaviorally beneficial organism.

SUMMARY OF THE INVENTION

The invention relates to a novel use of neuroactive compounds by treating the fruitfly *Drosophila melanogaster* adult males with fly medium containing either of the neuroactive compounds strychnine, pentylenetetrazol, tetraethylammonium chloride, lithium carbonate and nicotine, crossing the drug treated males with untreated females to obtain progenies and self-crossing the progenies to obtain grand progenies, observing the locomotor behavior of the parents and their progenies and grand progenies in terms of height climbed in a negative geotaxis assay, wherein an altered height climbed by parents and their progenies and grand progenies, compared to those of normally fed males, demonstrates that the neuroactive compounds produce inheritable behavioral change.

DETAILED DESCRIPTION OF THE INVENTION

Accordingly, present invention relates to a novel use of neuroactive drugs, the said method comprising (a) culturing *Drosophila melanogaster*,
(b) collecting flies of a single age group,
(c) separating males from females under ether anesthesia,
(d) treating the males of step (c) in the presence or absence of neuroactive drugs in the medium,
(e) subjecting the flies of step (d) to negative geotaxis,
(f) examining locomotor activity of flies of step (e) in terms of height climbed, wherein an alteration in height climbed in drug treated males, compared to that of normally fed flies, is characteristic of neuroactive compounds
(g) treating the males of step (f) in the absence of neuroactive drugs in the medium,
(h) crossing the males of step (d) with females never exposed earlier to any drug at any time to obtain F1 generation
(i) subjecting F1 flies to negative geotaxis,
(j) examining the height climbed by flies of step (i), wherein an altered locomotor activity is indicative of inheritance of altered behavior to F1 progenies,
(k) self-crossing the flies of step (h) to obtain F2,
(l) subjecting F2 flies to negative geotaxis assay,
(m) examining the height climbed by flies of step (i), wherein an altered locomotor activity is indicative of inheritance of altered behavior to F2 progenies.

In one embodiment of the invention, the neuroactive drugs used are selected from a group consisting of strychnine, pentylenetetrazol, tetraethylammonium chloride, lithium carbonate and nicotine.

Accordingly, the invention demonstrates that neuroactive drugs produce inheritable change in behavior wherein the drugs could be fed to male flies followed by observing an altered locomotor activity in flies, which were never exposed to any drug at any time, of the subsequent two generations that is characteristic of an inheritable effect of drugs. The neuroactive drugs to produce inheritable change in behavior may be selected from strychnine, pentylenetetrazol, tetraethylammonium chloride, lithium carbonate and nicotine.

BRIEF DESCRIPTION OF THE TABLE

TABLE 1: Height climbed by flies (in cm)

EXAMPLES

The invention is illustrated by the following examples, which are provided to illustrate the invention and should not be construed as limitation in the inventive concept herein.

Example 1

Unless otherwise mentioned, standard methods of fly manipulation were followed. Standard fly medium consisting of agar-agar, maize powder, brown sugar, dried yeast and nipagin was used. Flies were cultured at $22\pm1°$ C., 60% RH, and 12 hrs light (9 AM to 9 PM) and 12 hours dark cycle. *D. melanogaster* wild type Oregon-R strain was used in the experiment. To obtain males for control and drug treatment, flies from identical cultures grown in glass vials were first allowed to lay eggs in milk bottles containing medium. Flies were shifted to fresh bottles every 12 hr. First 4 sets of bottles were discarded. Flies that emerged in subsequent bottles were only used. Those that emerged in the beginning were first discarded and then flies were collected twice at 12 hr interval. Flies collected each time were kept separately in a single bottle. Two days after first collection, males and females from both the bottles were separated. Males were then pooled together and shifted to a new bottle. Flies were used for control or drug treatment two days later.

Example 2

Following morning after pooling males for treatment, drugs (Sigma-Aldrich Co, St. Louis, U.S.A.) were first dissolved in distilled water at following concentration: 33.3 mg/ml of strychnine (STR), 40 mg/ml of pentylenetetrazol (PTZ), 20 mg/ml of tetraethylammonium chloride (TEA), 10 mg/ml of lithium chloride (LICA) and 2 mg/ml of nicotine (NICO). Appropriate volume of freshly made drug solutions were then poured in molten fly media, and mixed thoroughly, to achieve a final concentration of 3.33 mg/ml of STR, 4 mg/ml of PTZ, 2 mg/ml of TEA, 1 mg/ml of LICA, and 0.2 mg/ml of NICO. For control, i.e., normal food (NF), distilled water of same volume as drug solution was added in the medium and mixed. Following this, the molten media was dispensed in glass vials, stored overnight at 4° C. and then used for above treatment of flies. Thirty male flies were shifted to each of the seven treatment vials, NF, STR, PTZ, TEA, LICA and NICO. Flies were maintained at $22\pm1°$ C., 60% RH, and 12 hrs light (9 AM to 9 PM) and 12 hours dark cycle.

Example 3

On $22^{nd}$ day of the beginning of drug treatment, three males from each treatment were separately mated to a single virgin female each. The females were grown on NF and were never exposed to any drug at any time. The F1 progenies resulting from each pair mating were pooled together before being further used. F2 generation was obtained through mating in mass the F1 progenies. F1 to F2 flies were never exposed to any drug at any time.

Example 4

Routine examination of gross locomotor behavior was carried out were at room temperature between 9 AM to 9 PM using startle induced group climbing test, by simultaneously tapping two treatment vials, one containing the control flies and the other, flies treated with either drug. The vials were tapped in inverted position, i.e., cotton side down, on a piece of packing foam so that all the flies are brought down at the bottom of the vial. Flies were then allowed to climb in inverted vials, standing undisturbed on the surface of the table. Climbing activities in the two vials were then visually compared to subjectively assess if there is any difference between the control and the drug groups. This exercise was repeated several times each in many sessions each day to arrive at either of the three possible alternatives—the drug groups climb faster than that of control, slower than that of control, or climb with a speed similar to that of control. During routine startle induced group climbing test, all the vials of a parallel set were similarly treated for same number of times. Drug vials were coded to eliminate any bias. In case of any doubt, several pairs of flies, a control and a drug fly in each pair, were separately examined. Also, drug-drug comparisons were often made for the same reason.

Example 5

Negative geotaxis assays for measuring height climbed and climbing speed, and horizontal locomotion assay for measuring distance walked—were performed at room temperature, between 9 AM to 9 PM. They were all performed at a specified area in a room, where same light sources were always used. While measuring various locomotor activities, extreme care was taken to ensure that the room is quiet, and the table onto which assays were performed undisturbed and vibration free. Utmost care was taken to ensure identical handling of flies, in minutest details. For measuring height climbed, climbing speed and distance walked, a single fly was randomly selected at a time. This was achieved by first inverting flies from a given treatment vial into an empty vial and then continuously and gently shaking and inverting both the vials in such a way that a single fly is finally trapped in the empty vial. Once trapped, all the three locomotor activities were measured using the same fly, height climbed, climbing speed and distance walked, in that order. One fly each from NF, STR, PTZ, PILO, TEA, LICA, and ESD, selected randomly, was first scored and then the same exercise was repeated for another two flies. Once a fly was scored for all the three locomotor activities, it was discarded. Flies were particularly checked for intact legs and wings, before they were used in negative geotaxis and horizontal locomotion assays.

Example 6

A glass tube of 1.7 cm diameter and 30 or 36 mm length, along with two cotton plugs were used in negative geotaxis and horizontal locomotion assays. The tube was length wise marked with lines at every cm. Three flies from each treatment were assayed. Each fly was assayed 10 times in succession. Each fly was first familiarized in the tube by keeping it for a minute in vertically or horizontally placed tube, before negative geotaxis or horizontal locomotion assay, respectively was performed. Both the height climbed and the climbing speed was measured in the negative geotaxis assay. Horizontal locomotion assay was performed for measuring distance walked. In negative geotaxis assay, a single fly was trapped inside the tube. The fly was brought to the bottom of the tube, by tapping the tube on a piece of packing foam. As soon as the fly had fallen on the cotton plug at the bottom, the tube was as such placed vertically on the surface of the work table. The height climbed by the fly in cm and the time taken to climb in sec were both recorded. Climbing was considered complete when the fly either touched the cotton plug at the top, fell to the bottom after climbing a certain height, or stopped after climbing to a certain height for more than approximately 5 sec. While climbing, flies sometimes, rarely though, jumped and/or took flights upwards or downwards. Unless these activities looked unusual, they were accepted. Spiral movement, uncommon though, during climbing was accepted. Downward movement, rare though, during climbing was also accepted, unless it continued for an unusually long time. Climbing to a height less than 7 cm was not considered in the assay. In horizontal locomotion assay, a singly fly was first brought to the middle of the tube by gentle shaking and then the fly was constantly monitored to count how many lines it walked across in a minute. Any single jump, short or long, was counted as one. Usually flies walked straight along the upper surface towards one end of the tube, explored there by moving around the inner periphery for some time, and then moved towards the other end, and so on. Though uncommon, they also walked along the lower surface, moved in a spiral fashion, explored much at one end, and stopped at times for shorter or longer duration. All these variations were accepted in the assay.

Males were selected as parents because of the relative ease with which they could be fed on drug containing medium. Females would have laid eggs that, unless unfertilized, would have given rise to larval activity. This would have made chronic drug treatment difficult. Males and females were used to collect individual flies' data in F1 and F2 respectively. This was done mainly because of two reasons. First, flies of these sexes, with history of drugs in parents and grandparents respectively, showed, in general, more pronounced, relative to the corresponding opposite sex, abnormality in gross locomotor behavior in routine testing of startle induced group climbing activity. Second, a tight schedule in the experiment demanded other observations to be given a priority. It is however important to note here that less pronounced abnormality in gross locomotor activity in routine group climbing test may not have necessarily meant less pronounced abnormality in individual flies' locomotor activity when assessed in the specific locomotor assay, the negative geotaxis assay. Particularly because diameter of the tube used for negative geotaxis assay was less than that of vials used for group climbing test. Climbing or walking in tube with greater curvature would have been relatively difficult and therefore would have expectedly uncovered more the locomotor abnormality. This was indeed experienced while examining flies' locomotor behavior.

Locomotor Activity in Drug Treated Parents

Routine examination of control and drug treated flies for gross locomotor behavior in startle-induced group climbing test showed an altered locomotor activity in flies exposed to neuroactive drugs. On day 13 of the beginning of treatment, individual flies were used in negative geotaxis assay to measure height climbed. Compared to normal food (NF), food containing strychnine (STR), pentylenetetrazol (PTZ), tetraethylammonium (TEA), lithium carbonate (LICA), and nicotine (NICO) caused an increase in the height climbed by drug exposed flies in negative geotaxis assay, as given in Table 1

TABLE 1

|  | NF | STR | PTZ | TEA | LICA | NICO |
|---|---|---|---|---|---|---|
| Parents |  |  |  |  |  |  |
| Mean | 20.86 | 28** | 25.66* | 32.4*** | 32.96*** | 32.16*** |
| SE | 1.37 | 1.76 | 1.65 | 1.21 | 1.4 | 1.44 |
| F1 |  |  |  |  |  |  |
| Mean | 22.63 |  |  |  |  | 10.86*** |
| SE | 1.59 |  |  |  |  | 0.64 |
| F1 |  |  |  |  |  |  |
| Mean | 25.1 | 16.56*** | 13*** | 12.43*** | 17.7*** |  |
| SE | 1.33 | 1.5 | 1.23 | 1 | 1.43 |  |
| F2 |  |  |  |  |  |  |
| Mean | 21.3 | 29.83*** | 27.16** | 29.46*** | 27.53** | 29.36*** |
| SE | 1.57 | 0.16 | 1.05 | 0.53 | 1.09 | 0.63 |

F1 NICO was assayed on $14^{th}$ and rest of the F1 on $31^{st}$ day of their emergence, as described in the text. Number of observation n=30. Student's t-test, unpaired, was applied to test the significance of difference between control and drug means. Astricks denote the level of significance; single, 5%; double, 1%; triple, 0.1%.

Locomotor Activity in F1 Generation

The F1 flies were routinely checked for a period of 30 days for gross locomotor activity in startle induced group climbing test. Four main observations were made. First, both males and females, after a few days of emergence, started exhibiting abnormal locomotor behavior compared to control. Second, male and female progeny of NICO parents presented the most spectacular scene—they mostly remained at the bottom of the vial. They also climbed very slowly in startle induced group climbing test. Third, female flies with parental history of drugs in general and NICO in particular, however, stopped showing the alterations in locomotor activity on $13^{th}$ day onwards. On $14^{th}$ day of emergence, individual NF and NICO F1 males were subjected to negative geotaxis assay. Routine observation was further continued. When the abnormal locomotor behavior in case of the rest of the drugs, in general, were found to be consistent, they were all, along with control, subjected to negative geotaxis assay on $31^{st}$ day. All flies with parental drug history climbed a lesser height in negative geotaxis assay (Table 1).

Locomotor Activity in F2 Generation

Two batches of F2 generations were obtained. First batch resulted from eggs laid by up to 2 days old flies that, as mentioned earlier, had not yet started showing locomotor effect of drugs. The second batch resulted from eggs laid by older flies showing altered behavior. Routine examination of gross locomotor activities of first batch of F2 flies till $7^{th}$ day of emergence did not reveal any effect of drug treatment in grandparents in startle induced group climbing test. These flies were excluded from the experiment. Two main observations were made during routine examination of second batch of F2 flies. First, flies with grandparental history of drugs started showing, in general, altered locomotor behavior from third day of emergence. Second, females, not males, consistently showed effect of drugs on group climbing activity. On $8^{th}$ day of emergence, individual F2 females were subjected to negative geotaxis assay. Grandparental exposure of all the drugs resulted in an increase in height climbed (Table 1).

The present investigation was preceded by a preliminary experiment in which similar conclusions about long lasting effect of drugs and inheritance of drug induced behavioral alteration was reached at. Moreover, also in the experiments described here, individual flies' data is in consonance with gross locomotor behavior observed in routine group climbing tests. Furthermore, as mentioned above, the spectacular difference between control and F1 NICO flies in spontaneous locomotor activity, for example, underscores the extent to which the altered locomotor behavior was inherited. The overall reliability of the present finding is therefore ensured. It is important to note here that control flies used to obtain the above results were routinely compared with another parallel set of control flies. No difference was however observed between these two sets of flies. Further evidence of reliability of data, for example, comes from the following individual flies' data obtained through negative geotaxis assay. Control parents on day 7 of the beginning of the treatment resulted in the value 20·96±1·52 (Table 1). The corresponding value obtained in case of another parallel control was 23·8±2.06. The difference between the two sets of control flies with respect to the locomotor behavior was insignificant ($p > 0.05$). The drugs used here are structurally different and act through a diversity of modes, as glycine-gated chloride channel antagonist, -aminobutyric acid antagonist, muscarinic acetylcholine receptor agonist, $K^+$ channel blocker, dopamine D2 receptor modulator, T-type $Ca^{++}$ channel blocker, and nicotinic acetylcholine receptor agonist, respectively. This shows that effect on locomotor behavior is a feature common to neuroactive drugs as a class. It is important to note here that many drugs used here are known to cause movement disorders in man (18). Like mammals, dopaminergic pathways in Drosophila play a role in modulating locomotor behavior in response to neuroactive drugs (17). The present results therefore show that these drugs in general are capable of affecting dopaminergic system. This highlights the integrative characteristics of the nervous system. Dopamine is known to play a role in cognitive functions and behavior, influencing learning, memory, intelligence as well as eating-, sleep- and sexual-behavior etc (19–23). Dopaminergic disturbances are also believed to underlie aggressive behavior and suicidal tendency (24,25). Role of dopamine in drug addiction is well established (26). A defective dopaminergic transmission has been implicated in various neurological and psychiatric disorders such as narcolepsy, schizophrenia, depression, and attention deficit hyperactivity disorder (27–29).

Flies of F1 to F2 generations were never exposed to any drug. An altered locomotor behavior was however found in them. This observation reveals a new phenomenon—that drug induced abnormality in brain function is inheritable. The drugs used are known not for their mutagenic activities. The observed inheritance therefore must have occurred through some epigenetic means. This notion is supported by the finding that all the drugs affected the same characteristic in subsequent generations. Although it is difficult to predict the exact mechanism of epigenetic inheritance observed, involvement of a nervous system-gametogenesis connectivity affecting regulation of gene expression and chromatin structure in gametes may possibly be hypothesized. It is possible that neuroactive drugs used in the present work might directly or indirectly, through their known effect on nervous system, affect expression of genes involved in neuronal function in the germ line. An indirect mode is more likely because the drugs were withdrawn long back before the parents were used in mating to generate F1. It is therefore the underlying neural plasticity, not drug, which is expected to maintain the stimulus necessary for inducing epigenetic change in the gametes around the time of fertilization. Inherent in this hypothesis is existence of a connection between nervous system and gametogenesis. It is interesting to speculate here, for example, a role of neuropeptides as a connecting link. These peptides regulate most, if not all, biological processes across animal species including Drosophila and humans (30). Neuropeptides are expressed by neurosecretory cells and may be released into the blood to act as neurohormones (31). Neuropeptides and their receptors are expressed in germ cells (32,33). Neuropeptide mediated synaptic plasticity is recently shown to involve regulation of gene expression and chromatin structure (12). It is possible that the present finding of inheritance of behavioral alteration induced by neuroactive drugs is mediated by epigenetic changes in the gametes caused through some kind of nervous system-gametogenesis axis. Although it is generally believed that genome is reprogrammed shortly after fertilization, recent evidence suggests that some epigenetic changes, in addition to those related to parentally imprinted genes, may bypass this route (5). Involvement of a nervous system-gametogenesis axis suggested here is further supported by the observed inheritance from F1 to F2 where no F1 and F2 fly was ever exposed to any drug. Additionally, routine examination of F1 to F2 flies detected alteration in their gross locomotor activity in startle induced group climbing test only after a few days of emergence. Eggs collected from F1 before this period gave rise to normal F2 flies showing no alteration in their gross locomotor behavior. This further lends support to the nervous system-gametogenesis axis hypothesis.

Advantages of the Invention

1. The novel use of neuroactive drugs in producing inheritable change in behavior provides for the first time a tool to produce non-genetically yet inheritably altered organism.
2. An epigenetic diversity of characteristics can be produced in the absence of availability of genetic diversity in the species.
3. Desirable behavioral characteristics can be potentially incorporated in an organism through appropriate breeding strategy.
4. Unlike genetically modified organism, epigenetically altered organism produced using the present strategy does not suffer from the serious concern about horizontal gene transfer and the associated hazard.

References

1. McLaren A, Chandler P, Buehr M, Fierz W, Simpson E. Immune reactivity of progeny of tetraparental male mice. *Nature* 1981; 290:513–14.
2. Gorczynski R M, Steele E J. Simultaneous yet independent inheritance of somatically acquired tolerance to two distinct H-2 antigenic haplotype determinants in mice. *Nature* 1981; 289:678–81.
3. Brent L, Chandler P, Fierz W, Medawar P B, Rayfield L S, Simpson E. Further studies on supposed lamarckian inheritance of immunological tolerance. *Nature* 1982; 295:242–44.

4. Rutherford S L, Henikoff S. Quantitative epigenetics. *Nat Genet.* 2003; 33:6–8.
5. Dennis C. Altered states. *Nature* 2003; 421:686–88.
6. Cavalli G, Paro R. Epigenetic inheritance of active chromatin after removal of the main transactivator. *Science* 1999; 286:955–58.
7. Sollars V, Lu X, Xiao L, Wang X, Garfinkel M D, Ruden D M. Evidence for an epigenetic mechanism by which Hsp90 acts as a capacitor for morphological evolution. *Nat Genet* 2003; 33:70–74.
8. Coyle J T, Duman R S. Finding the intracellular signaling pathways affected by mood disorder treatments. *Neuron* 2003; 38:157–160.
9. Gray N A, Zhou R, Du J, Moore G J, Manji H K. The use of mood stabilizers as plasticity enhancers in the treatment of neuropsychiatric disorders. *J. Clin. Psychiatry* 2003; 5:3–17.
10. Gerdeman G L, Partridge J G, Lupica C R, Lovinger D M. It could be habit forming: drugs of abuse and striatal synaptic plasticity. *Trends Neurosci.* 2003; 26:184–192.
11. Saal D, Dong Y, Bonci A, Malenka R C. Drugs of abuse and stress trigger a common synaptic adaptation in dopamine neurons. *Neuron* 2003; 37:577–582.
12. Guan Z, Giustetto M, Lomvardas S, Kim J H, Miniaci M C, Schwartz J H, Thanos D, Kandel E R. Integration of long-term-memory-related synaptic plasticity involves bidirectional regulation of gene expression and chromatin structure. *Cell* 2002; 111:483–493.
13. Andretic R, Chaney S, Hirsh J. Requirement of circadian genes for cocaine sensitization in *Drosophila*. *Science* 1999; 285:1066–68.
14. Wolf F W, Heberlein U. Invertebrate models of drug abuse. *J Neurobiol* 2003; 54:161–178.
15. Miller D K, Wilkins L H, Bardo M T, Crooks P A, Dwoskin L P. Once weekly administration of nicotine produces long-lasting locomotor sensitization in rats via a nicotinic receptor-mediated mechanism. *Psychopharmacology* 2001; 56:469–476.
16. Bevins R A, Besheer J. Individual differences in rat locomotor activity are diminished by nicotine through stimulation of central nicotinic acetylcholine receptors. *Physiol. Behav.* 2001; 72:237–244.
17. Bainton R J, Tsai L T, Singh C M, Moore M S, Neckameyer W S, Heberlein U. Dopamine modulates acute responses to cocaine, nicotine and ethanol in *Drosophila*. *Curr Biol* 2000; 10:187–194.
18. Blanchet P J. Antipsychotic drug-induced movement disorders. *Can J Neurol Sci* 2003; 30S1: S101-'7.
19. Mozley L H, Gur R C, Mozley P D, Gur R E. Striatal dopamine transporters and cognitive functioning in healthy men and women. *Am J Psychiatry* 2001; 158: 1492–99.
20. Setlow B, McGaugh J L. D2 dopamine receptor blockade immediately post-training enhances retention in hidden and visible platform versions of the water maze. *Learn Mem* 2000; 7:187–191.
21. Tsai S J, Yu Y W, Lin C H, Chen T J, Chen S P, Hong C J. Dopamine D2 receptor and N-methyl-D-aspartate receptor 2B subunit genetic variants and intelligence. *Neuropsychobiology* 2002; 45:128–30.
22. Bailer U F, Kaye W H. A review of neuropeptide and neuroendocrine dysregulation in anorexia and bulimia nervosa. *Curr Drug Target CNS Neurol Disod* 2003: 2:53–59.
23. de Saint Hilaire Z, Orosco M, Rouch C, Python A, Nicolaidis S. Neuromodulation of the prefrontal cortex during sleep: a microdialysis study in rats. *Neuroreport* 2000; 11:1619–24.
24. Miczek K A, Fish E W, De Bold J F, De Almeida R M. Social and neural determinants of aggressive behavior: pharmacotherapeutic targets at serotonin, dopamine and gamma-aminobutyric acid systems. *Psychopharmacology* 2002; 163:438–58.
25. Pitchot W, Hansenne M, Ansseau M. Role of dopamine in non-depressed patients with a history of suicide attempts. *Eur. Psychiatry* 2001; 16:424–27.
26. Phillips P E, Stuber G D, Heien M L, Wightman R M, Carelli R M. Subsecond dopamine release promotes cocaine seeking. *Nature* 2003; 422:614–18.
27. Eisensehr I, Linke R, Tatsch K, Von Lindeiner H, Kharraz B, Gildehaus F J, Eberle R, Pollmacher T, Schuld A, Noachtar S. Alteration of the striatal dopaminergic system in human narcolepsy. *Neurology* 2003; 60:1817–19.
28. Davids E, Zhang K, Tarazi F I, Baldessarini R J. Animal models of attention-deficit hyperactivity disorder. *Brain Res Brain Res Rev* 2003; 42:1–21.
29. Baumeister A A, Francis J L. Historical development of the dopamine hypothesis of schizophrenia. *J Hist Neurosci* 2002; 11:265–77.
30. Baggerman G, Cerstiaens A, De Loof A, Schoofs L. Peptidomics of the larval *Drosophila melanogaster* central nervous system. *J Biol Chem* 2002; 277: 40368–74.
31. Hewes R S, Snowdeal EC$3^{rd}$, Saitoe M, Taghert, P H. Functional redundancy of FMRFamide-related peptides at the *Drosophila* larval neuromuscular junction. *J. Neurosci* 1998; 18:7138–51.
32. Yoshikawa K, Aizawa T. Enkephalin precursor gene expression in postmeiotic germ cells. *Biochem Biophys Res Commun* 1988; 151:664–71.
33. Darboux I, Lingueglia E, Champigny G, Coscoy S, Barbry P, Lazdunski M. dGNaC1, a gonad-specific amiloride-sensitive Na+ channel. *J Biol Chem* 1998; 273:9424–29.

We claim:

1. A method for producing an inheritable change in locomotor behavior in *Drosophila melanogaster* comprising the steps of:
   a) culturing *Drosophila melanogaster* fruit flies;
   b) collecting 2 to 4 day old flies from the culture of step a);
   c) separating males and females obtained in step b);
   d) dividing the males into two groups and treating one group in the presence of a neuroactive drug in a medium comprising agar-agar, maize powder, brown sugar, dried yeast and nipagin and treating the second group in the absence of a neuroactive drug in a medium comprising agar-agar, maize powder, brown sugar, dried yeast and nipagin;
   e) subjecting the two groups of male flies of step d) to a negative geotaxis assay;
   f) examining locomotor activity of the two groups of male flies of step e) in terms of height climbed, wherein an alteration in height climbed in drug treated males compared to that of normally fed males is an effect of a neuroactive drug;
   g) further maintaining the two groups of male flies of step f) in a drug free medium;
   h) crossing separately the two groups of male flies of step g) with normal female fruit flies never exposed to any drug to obtain two groups of F1 flies;

i) subjecting the two groups of F1 flies of step h) to a negative geotaxis assay;

j) examining the height climbed by the two groups of F1 flies of step i), wherein an altered locomotor activity in F1 flies of drug exposed male flies relative to F1 flies of normally fed male flies is indicative of inheritance of altered behavior;

k) self-crossing separately each group of the F1 flies of step j) to obtain two groups of F2 flies;

l) subjecting the two groups of F2 flies of step k) to a negative geotaxis assay and m) examining the height climbed by the two groups of F2 flies of step I), wherein an altered locomotor activity in F2 flies of drug exposed male flies relative to F2 flies of normally fed male flies is indicative of inheritance of altered behavior.

* * * * *